United States Patent [19]
Lin et al.

[11] Patent Number: 5,994,135
[45] Date of Patent: *Nov. 30, 1999

[54] REGENERATION OF BOTH PLANT TISSUES AND TRANSGENIC PLANT TISSUES USING A NEW PLANT HORMONE, 5-BROMOINDOLE-3-ACETIC ACID

[75] Inventors: Jhy-Jhu Lin, Potomac; Jianqing Lan, Germantown; Nacyra Assad-Garcia, Gaithersburg, all of Md.

[73] Assignee: Life Technologies, Inc., Gaithersburg, Md.

[ * ] Notice: This patent is subject to a terminal disclaimer.

[21] Appl. No.: 08/861,666

[22] Filed: May 22, 1997

Related U.S. Application Data

[63] Continuation of application No. 08/430,209, Apr. 27, 1995, Pat. No. 5,674,731.

[51] Int. Cl.$^6$ ........................................... C12J 5/02
[52] U.S. Cl. ........................ 435/421; 435/425; 435/430; 435/430.1; 435/431; 504/136; 504/284
[58] Field of Search ..................... 435/421, 425, 435/430, 430.1, 431; 504/136, 284

[56] References Cited

U.S. PATENT DOCUMENTS

| | | |
|---|---|---|
| 3,000,888 | 9/1961 | Bierkert . |
| 4,297,125 | 10/1981 | Hassig et al. . |
| 4,411,684 | 10/1983 | Boyles et al. . |
| 4,455,162 | 6/1984 | Welebir . |
| 4,637,828 | 1/1987 | Schulze et al. . |
| 5,188,655 | 2/1993 | Jones et al. ............................. 504/136 |

OTHER PUBLICATIONS

Dekeyser, R.A. et al. (1990), "Transient Gene Expression in Intact and Organized Rice Tissues," Plant Cell 2:591–602.
Wang, Y–C, et al. (1988), "Transient expression of foreign genes in rice, wheat and soybean cells following particle bombardment," Plant Mol. Biol. 11:433–439.
Hooykaas–Van Slogteren, G.M.S. et al. (1984), "Expression of Ti plasmid genes in monocotyledonous plants infected with *Agrobacterium tumefaciens,*" Nature 311:763–764.
Rhodes et al. (1988), "Genetically Transformed Maize Plants from Protoplasts," Science 240:204–207.
Barton et al. (1983), "Regeneration of Intact Tobacco Plants Containing Full Length Copies of Genetically Engineered T–DNA, and Transmission of T–DNA to R1 Progeny," Cell 32:1033.
Abdullah et al. (1986), "Efficient Plant Regeneration from Rice Protoplasts Through Somatic Embryogenesis," Bio/Technology 6:1087–1090.
Böttger, M. et al. (1978), "Growth of Avena Coleoptiles and pH Drop of Protoplast Suspensions Induced by Chlorinated Indoleacetic Acids," Planta 140:89–92.
Skoog, F. and Tsui, C. (1951), "Growth Substances and the Formation of Buds in Plant Tissues," Plant Growth Substances, University of Wisconsin Press, Madison, WI, p. 263.

Rawal, S.K. and Mehta, A.R. (Dec. 1982), "Tissue Culture of Tobacco. II. Influence of IAA, Kinetin and Sucrose on Organogenesis in *Nicotiana Tabacum* Callus Cultures," Ind. J. Plant Physiol. XXV(4):336–347.
Skoog, F. and Miller, C.O. (1957), "Chemical Regulation of Growth and Organ Formation in Plant Tissues Cultured In Vitro," Symposia Soc. for Experimental Biology 11:188–231.
Porter, W.L. and Thimann, K.V. (1965), "Molecular Requirements for Auxin Action—I. Halogenated Indoles and Indoleacetic Acid," Phytochemistry, Pergamon Press Ltd., England 4:229–243.
Vetter, J. (1974), "The Auxin–induced Growth of Tobacco Callus Tissue," Biochem. Physiol. Pflanzen (BPP) 165:114–118.
Vanderhoef, L.N. et al. (1977), "Comparison of Auxin–induced and Acid–induced Elongation in Soybean Hypocotyl," Plant Physiol. 59:1004–1007.
Hatano, T. et al. (1987), "5,6–Dichloroindole–3–acetic acid as a potent auxin: its synthesis and biological activity," Experientia 43, Birkhauser Verlan, CH–4010, Basel, Switzerland, pp. 1237–1239.
Evans, M.L., "Functions of Hormones at the Cellular Level of Organization," Hormone Regulation of Development II. Encyclopedia of Plant Physiology, T.K. Scott (ed.), Springer Verlag, Heidelberg, pp. 23–78.
Saitou, T. et al. (1992), "Involvement of phytohormones in light–induced adventitious shoot formation of horseradish hairy roots," Plant Sci. 86:161–166.
Hoffmann, O.L. et al. (1952), "Auxin–Like Activity of Systematically Substituted Indoleacetic Acid," J. Biol. Chem. 196:437–441.
Rawal, S.K. and Mehta, A.R. (1982), "Tissue Culture of Tobacco. II. Influence of IAA, Kinetin and Sucrose on Organogenesis in *Nicotiana Tabacum* Callus Cultures," Ind. J. Plant Physiol. XXV(4):336–347.
Vasil, I.K. and Vasil, V. (1994), "In Vitro Culture of Cereals and Grasses," Plant Cell Tiss. Culture, pp. 293–312.
Lin, J. et al., "Effects of Agrobacterium Cell Concentration on the Transformation Efficiency of Tobacco and *Arabidopsis Thaliana,*" Focus 16(3):72–77.
Skoog, F. et al. (1967), "Cytokinins: Structure/Activity Relationships," Phytochemistry 6:1169–1192.

(List continued on next page.)

*Primary Examiner*—Leon B. Lankford, Jr.
*Attorney, Agent, or Firm*—Greenlee, Winner & Sullivan, P.C.

[57] ABSTRACT

The present invention describes the use of 5-bromoindole-3-acetic acid (5-B-IAA) as an auxin affecting plant cell growth. The invention relates to the use of 5-B-IAA compositions to affect growth in monocotyledonous as well as in dicotyledonous plants. The invention also describes the use of 5-B-IAA in plant growth affecting compositions for the regeneration of both plant tissues and transgenic plant tissues. Further, the invention provides plant growth affecting compositions comprising 5-B-IAA alone or in a mixture comprising one or more additional plant growth regulators, such as cytokinin, etc.

14 Claims, 2 Drawing Sheets

OTHER PUBLICATIONS

Chang, S.S. et al. (1994), "Stable genetic transformation of *Arabidopsis thaliana* by Agrobacterium inoculation in planta," Plant J. 5(4):551–558.

Jefferson, R.A. et al. (1987), "GUS fusions: β–glucuronidase as a sensitive and versatile gene fusion marker in higher plants," EMBO J. 6(13):3901–3907.

Rhodes, C.A. et al. (1988), "Plant Regeneration from Protoplasts Isolated from Embryogenic Maize Cell Cultures," Bio/Technology 6:56–60.

Raineri, D.M. et al. (1990), "Agrobacterium–mediated Transformation of Rice (*Oryza Sativa* L.)," Bio/Technology 8:33–38.

Winans, S.C. et al. (1988), Transcriptional Regulation of the virA and virG Genes of *Agrobacterium tumefaciens*, J. Bacteriol. 170(9):4047–4054.

Chilton, M–D. et al. (1974), "*Agrobacterium tumefaciens* DNA and PS8 Bacteriophase DNA Not Detected in Crown Gall Tumors," Proc. Natl. Acad. Sci. USA 71(9):3672–3676.

Vasil, I.K. (1988), "Progress in the Regeneration and Genetic Manipulation of Cereal Crops," Bio/Technology 6:397–402.

Hiei, Y. et al. (1994), "Efficient transformation of rice (*Oryza sativa* L.) mediated by Agrobacterium and sequence analysis of the boundaries of the T–DNA," Plant J. 6:001–011.

Aberg, B. (1978), "Plant growth regulators," Swedish J. Agric. Res. 8(3):133–138.

Altamura, M.M. et al. (1992), "The role of hormones on morphogenesis of thin layer explants from normal and transgenic tobacco plants," Physiol. Plant. 84:555–560.

Baldi, B.G. et al. (1984), "Synthesis of $^{14}$C–Labeled Halogen Substituted Indole–3–acetic Acids," J. Labelled Compounds and Radiopharmaceuticals XII(3):279–285.

Burns, J.A. and Schwarz, O.J. (1996), "Bacterial stimulation of adventitious rooting on in vitro cultured slash pine (*Pinus elliottii* Engelm) seedling explants," Plant Cell Rep. 15:405–408.

Chee, P.P. (1995),"Stimulation of adventitious rooting of Taxus species by thiamine," Plant Cell Rep. 14:753–757.

Cleland, R.E. (1995), "D1. Auxin and Cell Elongation," in *Plant Hormones*, P.J. Davies (ed.), Kluwer Academic Publishers, Netherlands, pp. 214–227.

Davies, P.J. (1995), "A1. The Plant Hormones: Their Nature, Occurrence, and Functions," in *Plant Hormones. Physiology, Biochemistry and Molelcular Biology*, 2$^{nd}$ Edition, P.J. Davies (ed.), Kluwer Academic Publishers, Norwell, MA, pp. 1–12.

Engvild, K. (1979), "Substituted indoleacetic acids tested in tissue cultures," Chemical Abstracts, 90(1), and Physiol. Plant (1978) 44(4):345–346.

Engvild, K.C. (1977), "Preparation of Chlorinated 3–Indolylacetic Acids," Acta Chem. Scand. B31:338–339.

Fox, S.W. and Bullock, M.W. (1951), "Synthesis of Indole–3–acetic Acids and 2–Carboxyindole–3–acetic Acids with Substituents in the Benzene Ring," J. Am. Chem. Soc. 73:2756–2759.

Katekar, G.F. and Geissler, A.E. (1982), "Auxins II: The Effect of Chlorinated Indolylacetic Acids on Pea Stems," Phytochemistry 21(2):257–260.

Katekar, G.F. and Geissler, A.E. (1983), "Structure–Activity Differences Between Indoleacetic Acid Auxins on Pea and Wheat," Phytochemistry 22(1):27–31.

Katayama, M. et al. (1988), "Localization of 4–Chloroindole–3–acetic Acid in Seeds of *Pisum sativum* and Its Absence from All Other Organs," Plant Cell Physiol. 29(5):889–891.

Lutz, B.T.G. et al. (1996), "FT–IR spectroscopic study of the phytohormone auxin (indole–3–ylacetic acid, IAA) and its n–alkylated and monohalogenated derivatives," J. Mol. Struct. 382(3):177–185.

Marumo et al. (1973), "Biological Activity of 4–chloroindolyl–3–acetic," Proc. 8$^{th}$ Int. Congr. Plant Growth Substances, Kirokawa Publ., Tokyo (1974), pp. 419–428.

Masanori, S., (Feb. 1984), Patent Abstracts of Japan, vol. 008, No. 024 (C–208), publication No. 58189161A.

Mihaljevic, S. et al. (1996), "Increase of root induction in *Pinus nigra* explants using agrobacteria," Plant Cell Rep. 15:610–614.

Mii, M. et al. (1992), "Shoot regeneration from spinach hypocotyl segments by short term treatment with 5,6–Dichloro–indole–3–acetic acid," Plant Cell Rep. 11:58–61.

Nilsson, O. et al. (1996), "Expression of the *Agrobacterium rhizogenes rolC* gene in a deciduous forest tree alters growth and development and leads to stem fasciation," Plant Physiol. 112:493–502.

Reinecke, D.M. et al. (1995), "Effect of halogen substitution of indole–3–acetic acid on biological activity in pea fruit," Phytochem. 40(5):1361–1366.

Rescher, U. et al. (1996), "In vitro binding affinities of 4–chloro–, 2–methyl–, 4–methyl–, and 4–ethylindoleacetic acid to auxin–binding protein 1 (ABP1) correlate with their growth–stimulating activities," J. Plant Growth Regualtion 15(1):1–3.

Schöpke, C. et al. (1996), "Regeneration of transgenic cassava plants (*Manihot esculenta* Crantz) from microbombarded embryogenic suspension cultures," Nature Biotechnology 14:731–735.

Thomson, A. et al. (1988), "The response of stomata to ring–substituted indolylacetic acids," New Phytol.110:511–515.

REGENERATION OF BOTH PLANT TISSUES AND TRANSGENIC PLANT TISSUES USING A NEW PLANT HORMONE, 5-BROMOINDOLE-3-ACETIC ACID

This application is a continuation of parent application U.S. Ser. No. 08/430,209 filed Apr. 27, 1995, now U.S. Pat. No. 5,674,731.

FIELD OF THE INVENTION

This invention relates to the use of 5-bromoindole-3-acetic acid (5-B-IAA) as a plant hormone stimulatory to cell growth. It particularly relates to the use of 5-B-IAA in plant growth affecting compositions for the regeneration of both plant tissues and transgenic plant tissues.

BACKGROUND OF THE INVENTION

Plant growth is affected by a variety of physical and chemical factors. Physical factors include available light, day length, moisture and temperature. Chemical factors include minerals, nitrates, cofactors, nutrient substances and plant growth regulators or hormones, for example, auxins, cytokinins and gibberellins.

Indole-3-acetic acid (IAA) is a naturally-occurring plant growth hormone identified in plants. IAA has been shown to be directly responsible for increase in growth in plants in vivo and in vitro. The characteristics influenced by IAA include cell elongation, internodal distance (height), leaf surface area and crop yield. IAA and other compounds exhibiting hormonal regulatory activity similar to that of IAA are included in a class of plant regulators called "auxins."

Compounds known to function as auxins in plants include, for example, 4-chloroindole-3-acetic acid (4-Cl-IAA) which is a naturally occurring plant growth regulator, acting to induce stem elongation and to promote root formation. Whereas IAA is found in most organs of a plant, 4-Cl-IAA was shown to be present in immature and mature seeds of Pisum sativum, but not in any other organ (Ulvskov et al. (1992) 188:182–189). Some synthetic auxins include naphthalene-1-acetic acid (NAA), 5,6-dichloro-indole-3-acetic acid (5,6-Cl$_2$-IAA), 4-chloro-2-methylphenoxyacetic acid (MCPA); 2,4-chlorophenoxyacetic acid (2,4D); 2,4,5-trichlorophenoxyacetic acid (2,4,5-T); 2-(4-chloro-2-methylphenoxy) propionic acid (CMPP); 4-(2,4-dichlorophenoxy) butyric acid (2,4-DB); 2,4,5-trichlorobenzoic acid (TBA); and 3,5-dichloro-2-methoxybenzoic acid (dicamba), for example. All the above acids are active in the form of their salts and esters, such as their sodium, potassium, ammonium, dimethylamine and ethanolamine salts, and their lower alkyl esters. Many of these synthetic auxins are being used commercially as effective herbicides and some of them are known to adversely affect morphogenesis of treated plants.

Preparations based on cytokinins, such as 6-furfurylamino purine (kinetin) and 6-benzylamino purine (BAP), are also known to be growth stimulators. However, cytokinin-based preparations are most effective in combination with auxins. While the mechanism by which cytokinins affect the growth cycle of plants is far from being understood, it is apparent that they affect leaf growth and prevent aging in certain plants.

It is a general objective in the field to successfully regenerate plants of major crop varieties using methods such as tissue culture and genetic engineering. The art of plant tissue culture has been an area of active research for many years but over the past five to ten years an intensified scientific effort has been made to develop regenerable plant tissue culture procedures for the important agricultural crops such as maize, wheat, rice, soybeans, and cotton.

In vitro culture techniques are well established in plant breeding (Reinert, J., and Bajaj, Y. P. S., eds. (1977) Plant Cell, Tissue and Organ Culture, Berlin: Springer; Simmonds, N. W. (1979) Principles of Crop Improvement, London: Longman; Vasil, I. K., Ahuja, M. K. and Vasil, V. (1979) "Plant tissue cultures in genetics and plant breeding," Adv. Genet. 20:127–215). First, embryo culture has, for decades, been a valuable adjunct to making difficult interspecific crosses. Second, more recent but also well established, is shoot-tip culture, which finds uses in rapid clonal multiplication, development of virus-free clones and genetic resource conservation work. Both techniques depend upon the retention of organizational integrity of the meristem. A step further takes us to callus, cell, and protoplast cultures in which organization is lost but can in most cases be recovered. A step further still takes us to in vitro hybridization, which has, after regeneration, yielded interspecific amphidiploids. The technique may provide desired amphidiploids which cannot be made by conventional means, and presents possibilities for somatic recombination by some variant of it. The foregoing techniques are widely in use (Chaleff, R. S. (1981) Genetics of Higher Plants, Applications of Cell Culture, Cambridge: Cambridge University Press).

Plant genetic engineering techniques enable the following steps: (a) identification of a specific gene; (b) isolation and cloning of the gene; (c) transfer of the gene to recipient plant host cells: (d) integration, transcription and translation of the DNA in the recipient cells; and (e) multiplication and use of the transgenic plant (T. Kosuge, C. P. Meredith and A. Hollaender, eds (1983) Genetic Engineering of Plants, 26:5–25; Rogers et al. (1988) Methods for Plant Molecular Biology [A. Weissbach and H. Weissbach, eds.] Academic Press, Inc., San Diego, Calif.). Newly inserted foreign genes have been shown to be stably maintained during plant regeneration and are transmitted to progeny as typical Mendelian traits (Horsch et al. (1984) Science 223:496, and DeBlock et al. (1984) EMBO 3:1681). The foreign genes retain their normal tissue specific and developmental expression patterns.

Successful transformation and regeneration techniques have been demonstrated in the prior art for many plant species. The Agrobacterium tumefaciens-mediated transformation system has proved to be efficient for many dicotyledonous plant species. For example, Barton et al. (1983, Cell 32:1033) reported the transformation and regeneration of tobacco plants, and Chang et al. (1994, Planta 5:551–558) described stable genetic transformation of Arabidopsis thaliana.

The Agrobacterium method for gene transfer was also applied to monocotyledonous plants, e.g.,in plants in the Liliaceae and Amaryllidaceae families (Hooykaas-Van Slogteren et al., 1984, Nature 311:763–764) and in Dioscorea bulbifera (yam) (Schafer et al., 1987, Nature 327:529–532); however, this method did not appear to be efficient for the transformation of graminaceous monocots, which include such food crops as wheat, rice and corn.

Transformation of food crops was obtained with alternative methods, e.g., by polyethylene glycol (PEG)-facilitated DNA uptake (Uchimiya et al. (1986) Mol. Gen. Genet. 204:204–207) and electroporation (Fromm et al. (1986) Nature 319:791–793), both of which used protoplasts as transfer targets. Monocot and dicot tissues may be transformed by bombardment of tissues by DNA-coated particles (Wang et al. (1988) Plant Mol. Biol. 11:433–439; Wu, in *Plant Biotechnology* (1989), Kung and Arntzen, Eds., Butterworth Publishers, Stoneham, Mass.). Regeneration was described in rice (Abdullah et al. (1986) Bio/Technology 4:1087–1090) and maize (Rhodes et al. (1988) Bio/Technology 6:56–60 and (1988) Science 240:204–207).

SUMMARY OF THE INVENTION

The principal object of the present invention is to provide a growth affecting composition comprising 5-bromoindole-3-acetic acid (5-B-IAA), or ester or salt derivatives of 5-B-IAA, in order to achieve a plant growth affecting response. The invention contemplates the use of 5-B-IAA to affect growth in both monocotyledonous and dicotyledonous plants.

It is also an object of the invention to provide a composition for affecting plant growth comprising a mixture of 5-B-IAA and one or more additional plant growth regulators, for example, a cytokinin, a gibberellin, etc., in definite proportions for wide application to various plants in order to achieve a plant growth affecting response. In specific embodiments, the invention was exemplified with compositions comprising 5-B-IAA and a cytokinin to affect the growth of plants.

It is a further object of the invention to provide a composition for affecting plant growth comprising 5-B-IAA or a mixture of 5-B-IAA and cytokinin as a component of media which sustain the plant during plant development or tissue regeneration and also serve as a vehicle whereby a 5-B-IAA-comprising composition may be applied.

It is an additional object of the invention to provide a method of affecting plant growth which comprises the step of applying an effective amount of the plant growth affecting composition comprising 5-B-IAA or a mixture of 5-B-IAA and one or more additional plant growth regulators, for example, a cytokinin, a gibberellin, etc., to a plant species, a plant locus, cell or tissue, or a seed of a plant. In specific embodiments, the invention was exemplified with compositions comprising 5-B-IAA and a cytokinin to affect the growth of plants.

Furthermore, it is an object of the invention to provide a method of affecting plant growth which comprises the step of applying an effective amount of the plant growth affecting composition comprising 5-B-IAA or a mixture of 5-B-IAA and one or more additional plant growth regulators, for example, a cytokinin, a gibberellin, etc., to a transgenic plant. In specific embodiments, the invention was exemplified with compositions comprising 5-B-IAA and a cytokinin to affect the growth of plants.

DETAILED DESCRIPTION OF THE INVENTION

The following definitions are provided in order to provide clarity as to the intent or scope of their usage in the specification and claims.

The term 5-bromoindole-3-acetic acid or 5-B-IAA as used herein refers not only to the free acid form but also to an amide, an ester or a salt form of 5-B-IAA. Included in the meaning of 5-B-IAA are, for example, such salt and ester derivatives as the sodium, potassium, ammonium, dimethylamine, ethanolamine, etc. salts and amides and the lower alkyl esters.

The term plant growth regulator or hormone as used herein refers to a naturally occurring or synthetic compound that acts as a hormone in regulating plant growth. Important growth regulators are exemplified by auxins, cytokinins and gibberellins.

The term auxin or cytokinin as used herein refers to a plant growth regulator that affects the growth of plants. An auxin is exemplified by a compound such as indole-3-acetic acid (IAA), indole-3-butyric acid (IBA), 2,4-dichlorophenoxyacetic acid (2,4-D), naphthaleneacetic acid (NAA), 5,6-dichloroindole-3-acetic acid (5,6-$Cl_2$-IAA) and the like. A cytokinin is exemplified by a compound such as 6-benzylamino purine (BAP), $N^{6}$ ($\Delta_2$ isopentenyl) adenine (2iP), isopentenylpyrophosphate (ipp), 6-(4-hydroxy-3-methyl-2-transbetenylamino)purine (zeatin), 6-furfurylaminopurine (kinetin) and the like. A compound can be tested for auxin activity using a bioassay, e.g., the elongation of coleoptiles of *Avena sativa* (Bottger et al. (1978) Planta 140:89) or the root growth inhibition of Chinese cabbage (Marumo et al. (1974) in *Plant Growth Substance*, p. 419, Hirokawa Publishing Co., Inc., Tokyo) or the hypocotyl swelling of mung bean (Marumo et al. (1974) supra). Cytokinin activity may be measured in assays designed to evaluate the promotion of growth in plants (e.g., tobacco bioassays, etc.) as is well known in the art (Skoog et al. 1967) Phytochem 6:1169–1192; Morris (1986) Ann. Rev. Plant Physiol. 37:509–538; Horgan (1984) in Advanced Plant Physiol (Wilkins, M. B., ed.) pp. 53–75, Pitman Publishing, London; Letham and Palni (1983) Ann. Rev. Plant Physiol 34:163–197; and Chen (1981) in *Metabolism and Molecular Activities of Cytokinins* (Guern, J. and Peaud-Lenoel, C., eds., Springer, New York, pp. 34–43). Variations of the cytokinin/auxin concentration ratio cause the enhancement in plant growth to occur preferentially in certain tissues. For example, a high cytokinin/auxin ratio promotes growth of shoots, whereas a low cytokinin to auxin ratio promotes the growth of roots (Depicker et al. (1983) in Genetic Engineering of Plants, T. Kosunge, C. P. Meredith and A. Hollaender, eds., Plenum Press, New York, p. 154).

The term a plant as used herein refers to a whole plant or a part of a plant comprising, for example, a locus of a plant, a cell of a plant, a tissue of a plant, an explant, or seeds of a plant. This term further contemplates a plant in the form of a suspension culture or a tissue culture including, but not limited to, a culture of calli, protoplasts, embryos, organs, organelles, etc.

The term transformed plant or transformed plant tissues as used herein refers to introduction of a foreign DNA into a plant or plant tissue and expression of the DNA in the plant or plant tissue.

The term transgenic plant or transgenic plant tissue as used herein refers to a plant or plant tissue stably transformed with a foreign gene introduced into the genome of the individual plant cells.

The term transient expression refers to a plant or plant tissue transformed with a DNA, where that DNA is expressed only for a short period of time immediately after transformation.

The term genetic engineering as used herein refers to the introduction of foreign, often chimeric, genes into one or more plant cells which can be regenerated into whole, sexually competent, viable plants which can be self-pollinated or cross-pollinated with other plants of the same species so that the foreign gene, carried in the germ line, can be inserted into or bred into agriculturally useful plant varieties.

The term regeneration as used herein refers to the production of at least one newly developed or regenerated plant tissue, e.g., root, shoot, callus, etc., from a cultured plant tissue or unit, e.g., leaf disc, seed, etc.

The terms percent regeneration, % regeneration or regeneration efficiency as used herein refer to the number of tissue cultured plant units producing at least one newly developed or regenerated tissue as a percentage of the total number of tissue cultured plant units, e.g., $$\left(\frac{\text{number of leaf discs with shoots}}{\text{total number of leaf discs}} \times 100\right).$$

The terms affecting plant growth or growth affecting or affector or affect as used herein refer to any one of a number of plant responses which improve or change, relative to what is observed in the absence of the growth regulator, some characteristic of overall plant growth, for example, stimulation of seed germination, inducing rooting, suppressing shooting, promoting cell proliferation, stimulating callus growth, etc.

The term effective amount as used herein refers to the amount or concentration of a compound that is a plant growth regulator or hormone administered to a plant such that the compound stimulates or invokes one or more of a variety of plant growth responses. A plant growth response includes, among others, the induction of stem elongation, the promotion of root formation, the stimulation of callus formation, enhancement of leaf growth, stimulation of seed germination, increase in the dry weight content of a number of plants and plant parts, and the like.

The present invention relates to the discovery that 5-B-IAA, a chemically synthesized compound that is commercially available, has utility as an auxin in affecting plant growth. (Of eleven commercially available IAA analogs tested for tobacco plant growth regulatory activity, only 5-B-IAA exhibited the ability to stimulate root and callus formation. In combining 5-B-IAA with cytokinin, both callus and shoot formation were observed.

5-B-IAA was found to be superior to IAA in functioning as an auxin in both monocots and dicots. For example, 5-B-IAA was between two and four times more effective than IAA in stimulating the regeneration of green calli from *Arabidopsis thaliana*. The effect of 5-B-IAA is all the more remarkable in light of the prior art teaching for Arabidopsis tissue culture responses that "callus induction and regeneration frequencies are high for root, lower for anther and stem and lowest for leaf explants." In accordance with the present invention, 5-B-IAA gave an efficiency of 100% for regeneration from *Arabidopsis thaliana* leaves.

Superiority of 5-B-IAA was also observed in monocot regeneration. Prior art methods used to obtain tissue regeneration from monocotyledonous plants, for example, rice, require approximately three months and incubation of immature seeds in two different culture media. In contrast, in accordance with the present invention using 5-B-IAA as auxin, regeneration of shoots from rice embryonic callus derived from mature seeds was obtained in about one and a half months, requiring only one incubation medium comprising 5-B-IAA and a cytokinin (e.g., BAP) and yielding a regeneration efficiency of 100%. In all bioassays performed to show regeneration from plant tissue and from transgenic plant tissue, 5-B-IAA functioned as an auxin to stimulate growth at least as well as, and in many cases better than, IAA, the auxin standard of the art.

Growth affecting compositions of the present invention comprise 5-B-IAA, or a mixture of 5-B-IAA and one or more additional plant growth regulators, such as cytokinin, gibberellin or the like, mixed with a carrier or auxiliary nutrients. The use of BAP, 2iP and kinetin has been exemplified in particular embodiments of this invention. It is contemplated that other cytokinins or other plant growth regulators known to the art can be utilized with 5-B-IAA to make a growth affecting composition of the invention. It is also contemplated that more than one cytokinin or a different plant growth regulator (e.g., gibberellin, etc.) can be admixed with 5-B-IAA to make a growth enhancing composition of the invention. Also, the choice of plant growth regulator can be varied at different stages of the incubation or application cycles characterizing the growth of a particular plant. Plant growth regulators are known to the art and include, but are not limited to, BAP, 2iP, ipp, zeatin, kinetin, gibberellin, and the like, as described in Skoog et al. (1967) Phytochemistry 6:1169–1192 and Theologis (1989) in *Plant Biotechnology* (Kung and Arntzen, eds.) Butterworth Publishers, Stoneham, Mass.

The mechanism by which compositions comprising 5-B-IAA of the present invention effect the growth cycle of plants and plant tissues is not fully understood at present but it is apparent, as will be demonstrated hereinafter, that they play a significant role in inducing a number of growth affecting responses in a variety of plant species.

The practice of the present invention contemplates a wide variety of plant growth responses, including stimulation of seed germination and breaking of dormancy; increasing yields; hastening ripening and color production in fruit; increasing flowering and fruiting; stimulating shoot formation; inducing callus development; inducing rooting and causing cell proliferation; increasing the hardiness of various plant species; and increasing the dry weight content of a number of plants and plant parts. In addition to these categories of responses, any other modification of a plant, seed, fruit or vegetable, so long as the net result is to increase the growth or maximize any beneficial or desired property of the agricultural and horticultural crop or seed, is intended to be included within the scope of advantageous responses achieved by the practice of the present invention.

Suitable applications of the growth enhancing compositions of the present invention to cultures of plant tissues were shown to induce the regeneration of shoots, roots or calli. This effect was exemplified in both monocotyledonous and dicotyledonous plant species and is applicable to a wide variety of plants.

The compositions of the instant invention were further utilized for plant regeneration from transgenic plants.

Genetic engineering of plants generally involves two complementary processes. The first process involves the genetic transformation of one or more plant cells of a specifically characterized type. By transformation it is meant that a foreign gene, typically a chimeric gene construct, is introduced into the genome of the individual plant cells, typically through the aid of a vector which has the ability to transfer the gene of interest into the genome of the plant cells in culture. The second process then involves the regeneration of the transformed plant cells into whole sexually competent plants. Neither the transformation nor regeneration process need be 100% successful but must have a reasonable degree of reliability and reproducibility so that a reasonable percentage of the cells can be transformed and regenerated into whole plants.

The two processes, transformation and regeneration, must be complementary. The complementarity of the two processes must be such that the tissues which are successfully genetically transformed by the transformation process must be of a type and character, and must be in sufficient health, competency and vitality, so that they can be successfully regenerated into whole plants.

Successful transformation and regeneration techniques have been demonstrated for monocots and dicots in the prior art. For example, the transformation and regeneration of tobacco plants was reported in Barton et al., Cell 32:1033 (April 1983), whereas the regeneration of cotton is described in Umbeck, U.S. Pat. No. 5,004,863, issued Apr. 2, 1991. Further, transformation and regeneration of rice was described by Abdullah et al. (1986) Bio/Technology 4:1087–1090, whereas maize was transformed and regenerated as described in Rhodes et al. (1988) Bio/Technology 6:56–60 and Science 240:204–207.

The most common methodology used for the transformation of cells of dicot plant species involves the use of the plant pathogen *Agrobacterium tumefaciens*. Although Agrobacterium-mediated transformation has been achieved in some monocots, other methods of gene transfer have been more effective, e.g., the polyethylene glycol method, electroporation, direct injection, particle bombardment, etc., as described by Wu in *Plant Biotechnology* (1989) pp. 35–51, Butterworth Publishers, Stoneham, Mass. The present invention will be useful with any method of transformation that includes plant regeneration steps.

In a specific embodiment, the invention envisions the genetic transformation of tissues in culture derived from leaf discs or hypocotyl explants. The transformed tissues can be induced to form plant tissue structures, which can be regenerated into whole plants.

The transformation technique of the present invention is one which makes use of the Ti plasmid of *A. tumefaciens*. In using an *A. tumefaciens* culture as a transformation vehicle, it is most advantageous to use a non-oncogenic strain of the Agrobacterium as the vector carrier so that normal non-oncogenic differentiation of the transformed tissue is possible. To be effective once introduced into plant cells, the chimeric construction including a foreign gene of interest must contain a promoter which is effective in plant cells to cause transcription of the gene of interest and a polyadenylation sequence or transcription control sequence also recognized in plant cells. Promoters known to be effective in plant cells include the nopaline synthase promoter, isolated from the T-DNA of Agrobacterium, and the cauliflower mosaic virus 35S promoter. Other suitable promoters are known in the art. It is also preferred that the vector which harbors the foreign gene of interest also contain therein one or more selectable marker genes so that the transformed cells can be selected from non-transformed cells in culture. In many applications, preferred marker genes include antibiotic resistance genes so that the appropriate antibiotic can be used to segregate and select for transformed cells from among cells which are not transformed.

The details of the construction of the vectors containing such foreign genes of interest are known to those skilled in the art of plant genetic engineering and do not differ in kind from those practices which have previously been demonstrated to be effective in tobacco, petunia and other model plant species. The foreign gene should obviously be selected as a marker gene (Jefferson et al. (1987) EMBO J. 6:3901–3907) or to accomplish some desirable effect in plant cells. This effect may be growth promotion, disease resistance, a change in plant morphology or plant product quality, or any other change which can be accomplished by genetic manipulation. The chimeric gene construction can code for the expression of one or more exogenous proteins, or can cause the transcription of negative strand RNAs to control or inhibit either a disease process or an undesirable endogenous plant function.

To initiate the transformation and regeneration process for plant tissues, it is necessary to first surface sterilize tissues to prevent inadvertent contamination of the resulting culture. If the tissues are seeds, the seeds are then allowed to germinate on an appropriate germinating medium containing a fungicide. Four to ten days after germination the hypocotyl portion of the immature plant is removed and sectioned into small segments averaging approximately 0.5 centimeters apiece. The hypocotyl explants are allowed to stabilize and remain viable in a liquid or agar plant tissue culture medium.

Once the tissues have stabilized, they can promptly be inoculated with a suspension culture of transformation competent non-oncogenic Agrobacterium. The inoculation process is allowed to proceed for a short period, e.g., two days, at room temperature, i.e., 24° C.

At the end of the inoculation time period, the remaining treated tissues can be transferred to a selective agar medium, which contains one or more antibiotics toxic to Agrobacterium but not to plant tissues, at a concentration sufficient to kill any Agrobacterium remaining in the culture. Suitable antibiotics for use in such a medium include carbenicillin cefotaxime, etc. as the bacteriocide for Agrobacterium and kanamycin as the selective antibiotic for transformed plant tissues.

The tissues are now cultivated on a tissue culture medium which, in addition to its normal components, contains a selection agent. The selection agent, exemplified herein by kanamycin, is toxic to non-transformed cells but not to transformed cells which have incorporated genetic resistance to the selection agent and are expressing that resistance. A suitable tissue culture medium is the MS medium to which is added the phytohormones 5-B-IAA and a cytokinin, with or without antibiotics. The surviving transformed tissues are transferred to a secondary medium to induce tissue regeneration. The surviving transformed tissue will thus continue to be regenerated into a whole plant through the regeneration technique of the present invention or through any other alternative plant regeneration protocols.

The precise amount of growth affecting compositions employed in the practice of the present invention will depend upon the type of response desired, the formulation used and the type of plant treated. The invention contemplates the use of a ratio of cytokinin concentration to auxin concentration of between approximately 50.0 and 0.001, and preferably between approximately 5.0 and 0.05, and more preferably between approximately 2.0 and 0.25.

The chemical compounds employed as active components of the growth enhancing compositions of the present invention may be prepared in accordance with processes well known in the prior art or may be obtained commercially from readily available sources.

The present compositions may be applied at any developmental stage of the plant species to obtain plant hormone or maintenance effects throughout maturity and to expedite regrowth in damaged tissues during early developmental stages, depending upon the concentration used, the formulation employed and the type of plant species treated.

The compositions of the present invention are preferably used in conjunction with specific auxiliary nutrients or other plant growth regulators in precise proportions to achieve a particular synergistic, growth enhancing response in various type of plants. The present compositions may additionally be used in association with fungicides to increase the disease resistance of various plants, making the plant tissue resistant to invasion by pathogens by influencing the enzyme and plant processes which regulate natural disease immunity. While the present compositions possess essentially no phytotoxic activity of their own, they may sometimes be used in conjunction with herbicides to stimulate the growth of unwanted plants in order to make such plants more susceptible to a herbicide. However, it is preferred to regard the results achieved in the practice of the present invention as growth enhancing responses in agricultural and horticultural crops, as well as perennial and annual household plants species.

The following examples are illustrative of the wide range of plant growth responses that can be realized by application of a preferred composition of the present invention to various plant species. Nevertheless, there is no intention that the invention be limited to these optimum ratios of active components since workers in the art will find the compositions of the invention set forth hereinabove to be effective growth enhancers. Also, it should readily occur to one skilled in the art that the recognition of improved results using the compositions according to the present invention in connection with other plants, seeds, fruits and vegetables not specifically illustrated herein is readily within the capabilities of one skilled in the art. The following examples serve to illustrate the utility of the invention without limiting its scope.

EXAMPLES

Example 1
Evaluation of Auxin Activity in Tobacco

Seeds of *Nicotiana tobaccum* Xanthi were provided by Dr. James Saunders (USDA, Beltsville, Md.). Young tobacco leaves were removed and cut into small pieces. The explants were incubated on (1) MS complete medium containing different concentrations of auxin related compounds only or (2) MS complete medium containing different concentrations of auxin-related compounds and 0.5 mg/l benzylaminopurine (BAP) using an 18 h light/6 h dark cycle until the formation of green calli and shoots.

The regeneration of plant tissues using tissue culture depends on plant hormones such as auxin and cytokinin. It is known that the presence of an auxin in plant tissue cultured on Murashige and Skoog (MS) medium (Murashige, T. and F. Skoog (1962) Physiol. Plant 15:473–497) stimulates the formation of root structure whereas the formation of callus is observed when not only the auxin but also a cytokinin complement the MS nutrient medium. Therefore, evaluation of a test compound as a potential new auxin was performed by incubating tobacco leaf discs in (a) the MS complete medium containing different concentrations of auxin only and (b) the MS complete medium containing different ratios of cytokinin to auxin concentrations (cytokinin/auxin).

Thirteen commercially available compounds were tested for plant growth regulatory activity. As shown in Table 1, only 5-B-IAA exhibited the ability to stimulate root and shoot formation. Different concentrations of each compound were tested for the ability to stimulate root formation from tobacco leaf discs. The ability to stimulate root formation was evaluated for each compound in the presence of different concentration ratios of cytokinin (BAP) to test compound.

TABLE 1

Evaluation of different test compounds for auxin activity using tobacco leaf disc.

| | Regeneration from Tobacco Leaf Discs | | | | | |
|---|---|---|---|---|---|---|
| | Root Formation Test Compound (mg/l) | | | Callus Formation Ratio of BAP/Test compound | | |
| Test Compounds | 0.5 | 1.0 | 2.0 | 2.0 | 1.0 | 0.5 |
| $N_\alpha$-acetyl-L-histidine monohydrate | – | – | – | – | – | – |
| (+)-6-aminopenicilianic acid | – | – | – | – | – | – |
| DL-α-amino-2-thiopheneacetic acid | – | – | – | – | – | – |
| 5-chloroindole-2-carboxylic acid | – | – | – | – | – | – |
| 2-furanacrylic acid | – | – | – | – | – | – |
| 5-hydroxyindole-3-acetic acid | – | – | – | – | – | – |
| 5-hydroxy-2-indolecaiboxylic acid | – | – | – | – | – | – |
| (±)-3-oxo-1-indancarboxylic acid | – | – | – | – | – | – |
| (R)-(-)-2-phenylglycine | – | – | – | – | – | – |
| (S)-(+)-2-2phenylglycine | – | – | – | – | – | – |
| 5-bromoindole-3-acetic acid | +++ | +++ | +++ | +++ | +++ | +++ |

+++ indicates stimulatory activity
– indicates no activity

Figure 1:
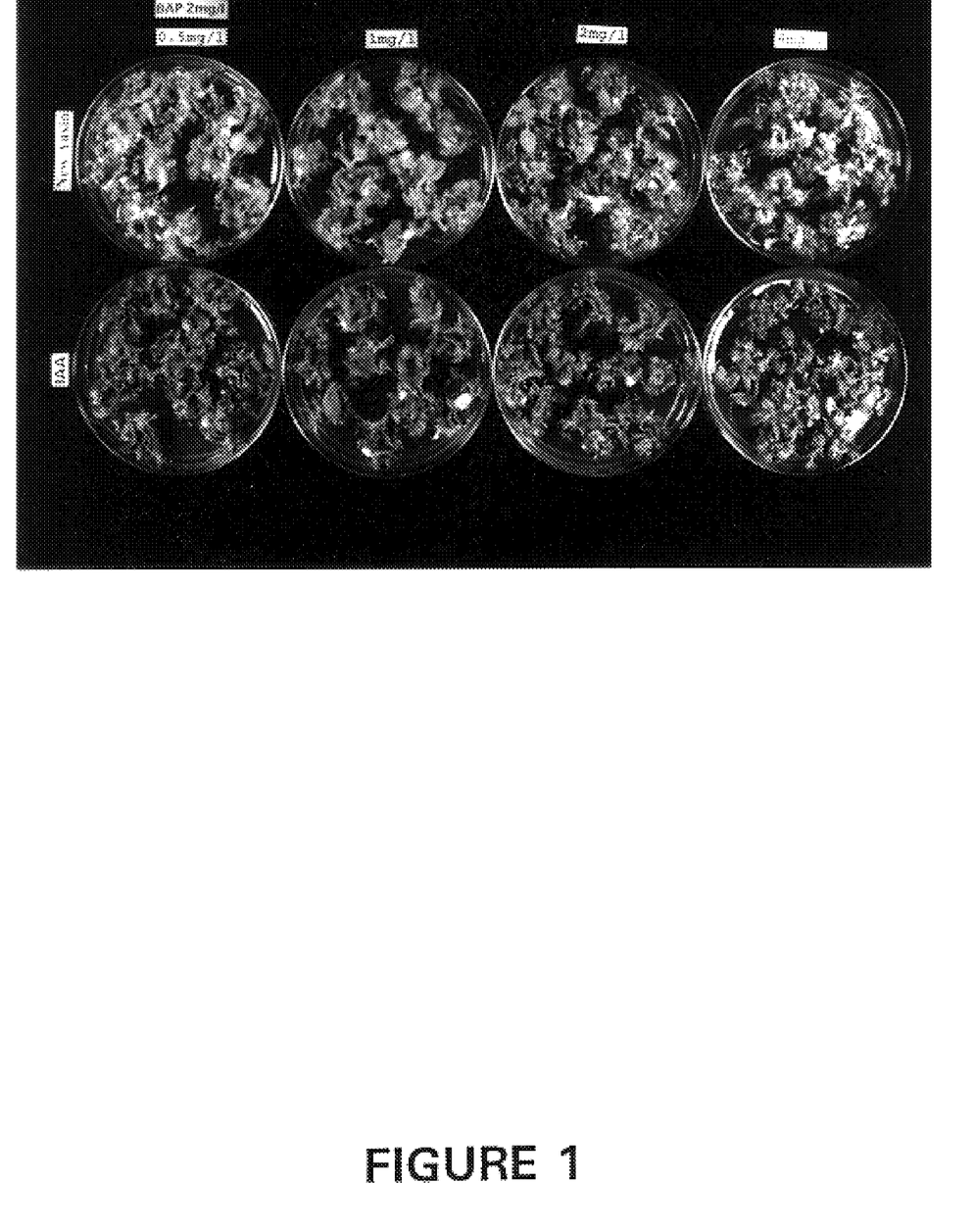
FIG. 1 documents plant growth stimulated by 5-B-IAA or IAA in the presence of different concentrations of BAP on the formation of root, shoots and calli. New Auxin=5-B-IAA.
Figure 2:
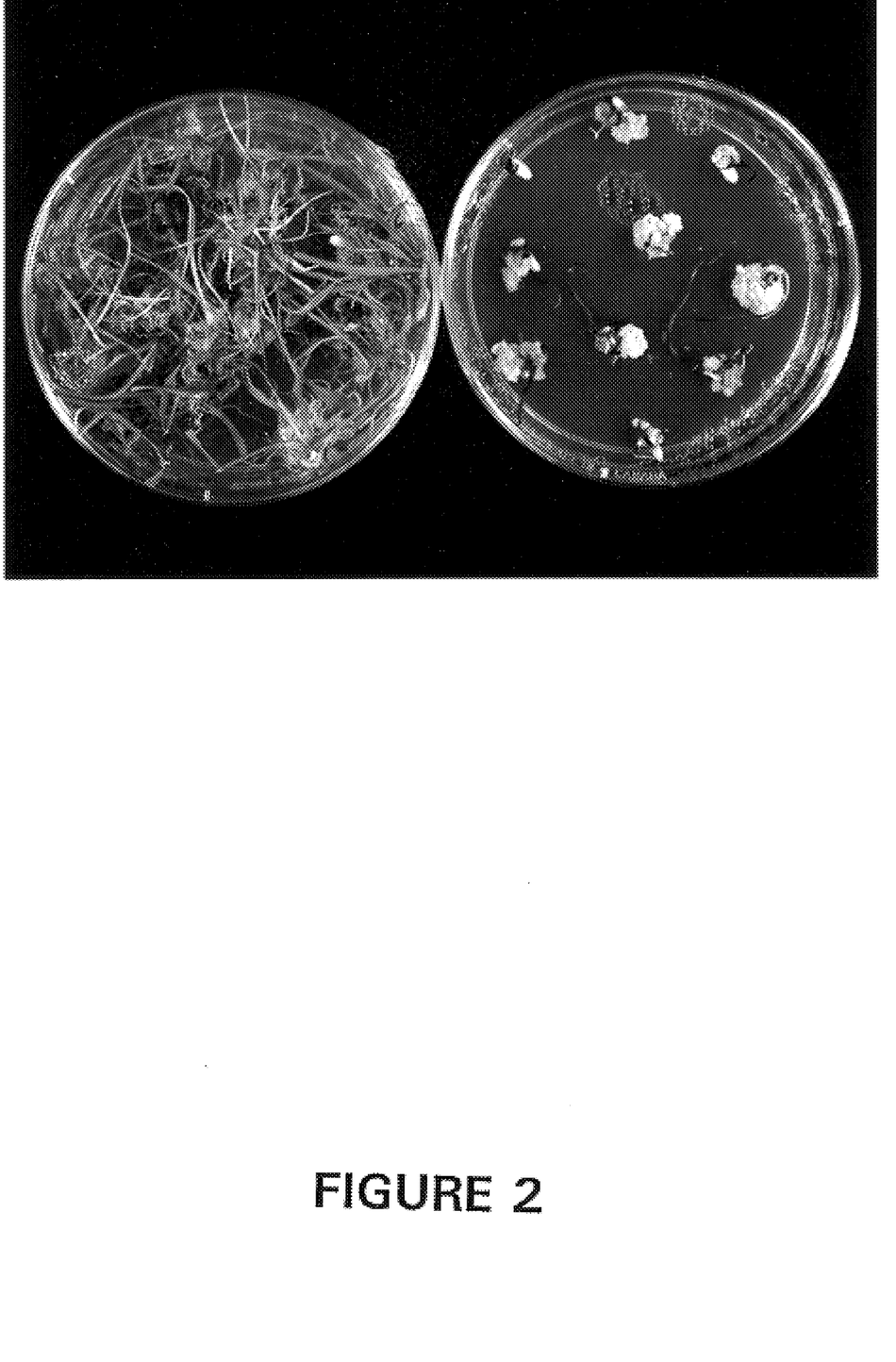
FIG. 2 presents the regeneration of embryogenic callus from mature seeds of *Oryza sativa* cv. Orion stimulated in a first medium comprising 2,4-D (left) and in a second medium comprising 5-B-IAA and BAP (right).

FIG. 1 demonstrates that 5-B-IAA functions as an effective auxin. Tobacco leaf discs grown on MS complete medium containing 5-B-IAA or IAA in the presence of low cytokinin concentrations demonstrated root formation, whereas tobacco leaf discs grown on MS complete medium containing 5-B-IAA and higher cytokinin (BAP) concentrations exhibited callus formation.

Example 2
Evaluation of 5-B-IAA Auxin Activity in *Arabidopsis thaliana*

Seeds of *Arabidopsis thaliana* ecotypes Columbia and Landersberg ereta were provided by Dr. Keith Davis (The Ohio State University, Columbus). Tissues of hypocotyl were removed from 10-day-old seedlings, transferred to MS complete medium containing (1) different concentrations of IAA or 5-B-IAA with different concentrations of $N^{6-}$ ($\Delta_2$Isopentenyl) adenine (2iP) and (2) different concentrations of 5-B-IAA with different concentrations of 2iP, BAP, or kinetin. The explants were incubated at 23° C. using an 18 h light/6 h dark cycle until the formation of green calli and shoots.

5-B-IAA was found to be effective in promoting the regeneration of green callus from *Arabidopsis thaliana* Columbia and Landersberg. Tissue cultures of *A. thaliana* leaves removed from 21-day-old seedlings were grown on MS medium comprising either IAA or 5-B-IAA and the cytokinin, 2iP. The concentrations of both auxin and cytokinin were varied as shown in Table 2.

TABLE 2

Effect of 5-bromoindole-3-acetic acid
on the regeneration of green callus from
*Arabidopsis thaliana* Columbia leaves

| Conc. of 2iP (mg/l) | Type of auxin | % regeneration of green callus Concentration of auxin (mg/l) | | | |
|---|---|---|---|---|---|
| | | 0.5 | 1.0 | 2.0 | 4.0 |
| 0.5 | IAA | 25.0 | 58.3 | 33.3 | 25.0 |
| 0.5 | 5-B-IAA | 50.0 | 100 | 83.3 | 91.6 |
| 2.0 | IAA | 23.0 | 33.3 | 25.0 | 25.0 |
| 2.0 | 5-B-IAA | 58.3 | 83.3 | 100 | 90.9 |

As indicated in Table 2, at all concentrations of auxin and cytokinin tested, 5-B-IAA was superior to IAA in stimulating the regeneration of green calli. Notably, an 100% regeneration efficiency of green callus was obtained using 5-B-IAA (see Table 2). In contrast, only low regeneration efficiencies have been reported (Koncz et al., (1992) Methods in Arabidopus Research, pp. 224–273) for the regeneration of green callus from *A. thaliana* using auxins such as IAA, 2,4-D or NAA.

Further, the effect of 5-B-IAA on the regeneration of green callus was tested in the presence of other cytokinins. As documented in Table 3, a high efficiency of regeneration was observed for 5-B-IAA with each of the three cytokinins tested, i.e., kinetin, 2iP and BAP. Moreover, 100% regeneration efficiencies were achieved for 5-B-IAA in the presence of kinetin as well as 2iP. Ratios of cytokinin to auxin of between 2.0 and 0.5 were found to be particularly effective.

TABLE 3

Effect of different cytokinins and
5-bromoindole-3-acetic acid on the regeneration of
green callus from *A. thalaianas* Columbia leaves

| Type of cytokinin | % regeneration of green callus Ratio of Cytokinin/5-B-IAA | | |
|---|---|---|---|
| | 2.0 | 1.0 | 0.5 |
| Kinetin | 90% | 100% | 100% |
| 2iP | 100% | 100% | 100% |
| BAP | 70% | 90% | 80% |

Example 3
Evaluation of 5-B-IAA Auxin Activity in Rice

Seeds of *Oryza sativa* cv. Orion were kindly provided by Dr. James Saunders (USDA, Beltsville, Md.). For rice embryogenic callus formation, the surfaces of the seeds were sterilized as follows: mature seeds were soaked in 0.5% detergent with shaking for 1 h, transferred to a solution containing 20% bleach and 0.1% Tween20® and vacuumed with shaking. The seeds were then rinsed with sterilized distilled water three times. At this point the seeds were transferred onto a MS complete medium containing different concentrations of BAP and different concentrations of 5-B-IAA, incubated in the dark at 25° C. for 1 month, and then incubated at 25° C. using an 18 h light/6 h dark cycle until the formation of green calli and shoots.

5-B-IAA was found to be effective on the regeneration of embryogenic callus from seeds of a monocotyledonous plant, e.g., rice. Tissue regeneration from monocotyledons is known to be a challenge with respect to regeneration efficiency as well as incubation time. For example, in rice, in order to obtain regenerated shoots from embryogenic calli, it takes approximately three months and requires incubation of cultures in two different media (MS complete medium containing 2,4-D and MS complete medium containing IAA and BAP).

In accordance with this invention, washed seeds of *Oryza sativa* cv. Orion were incubated on MS complete medium comprising BAP and different concentrations of 5-B-IAA. As shown in Table 4,

TABLE 4

Effect of 5-bromoindole-3-acetic acid
on the regeneration of embryogenic green callus
from seeds of *Oryza sativa* cv. Orion.

| Conc. of BAP (mg/l) | % regeneration of embryogenic callus Concentration of 5-B-IAA (mg/l) | | | |
|---|---|---|---|---|
| | 1.0 | 2.0 | 4.0 | 8.0 |
| 0.5 | — | 33% | 100% | 90% |
| 1.0 | 28% | 55% | 100% | — |
| 2.0 | 12% | 57% | 55% | — | shoot regeneration was obtained with 5-B-IAA at concentrations of approximately between 2.0 and 8.0 mg/l in the presence of BAP at concentrations of approximately between 0.5 and 2.0 mg/l. Notably, shoot regeneration from embryogenic callus was observed after only approximately one and a half months in culture and upon incubation in only one nutrient medium, i.e., an MS complete medium containing 5-B-IAA and BAP. Moreover, under these conditions with 5-B-IAA, an efficiency of 100% was achieved for shoot regeneration from embryogenic callus of a monocotyledonous plant as shown in Table 4.

Example 4
The use of 5-B-IAA for Stimulating the Regeneration of Transgenic Plants a) Tobacco Plant transformation was carried out according to the Agrobacterium-mediated transformation procedure essentially as described by Lin et al. [(1994) Focus 16:72–77)].

For tobacco, the leaf discs were incubated with $10^{10}$ cells/ml *Agrobacterium tumefaciens* LBA4404 cells, containing pBI121 harboring the GUS reporter gene, in MS complete medium with 0.5 mg/l 2-(N-morpholino) ethanesulfonic acid (MES) for 10 min, transferred to solid MS complete medium, and incubated for 2 days at 25° C., using an 18 h light/6 h dark cycle for cocultivation. After cocultivation, the explants were transferred to MS media containing different ratios of BAP/IAA or BAP/5-B-IAA, 100 mg/l kanamycin and 500 mg/l carbenicillin and incubated at 25° C. using an 18 h light/6 h dark cycle for shoot formation.

5-B-IAA was found to be effective in stimulating the regeneration of shoots from transgenic tobacco. Transformation of tobacco was confirmed by measuring GUS activity (Jefferson et al., Embo J. (1987) 6:3801–3807). A high transformation efficiency (80–100%) for transgenic tobacco plants containing GUS gene activity was easily achieved using high concentrations of *A. tumefaciens* LBA4404. Transformed tobacco was incubated in MS medium comprising BAP and either IAA or 5-B-IAA to promote shoot regeneration. As shown in Table 5, both IAA and 5-B-IAA were effective in stimulating shoot regeneration from transgenic tobacco.

TABLE 5

Effect of 5-bromoindole-3-acetic acid on the regeneration of shoots from Agrobacterium infected tobacco.

| Type of auxin | % regeneration of shoot Ratio of BAP/auxin | | | |
|---|---|---|---|---|
| | 2.0 | 1.0 | 0.5 | 0.25 |
| IAA | 100% | 80% | 90% | 90% |
| 5-B-IAA | 80% | 80% | 90% | 100% |

Within a range of BAP/auxin concentration ratios of between approximately 2.0 and 0.25, the efficiency of shoot regeneration from transgenic tobacco approached 100%, ranging from approximately 80–100%, as shown in Table 5.

b) *Arabidopsis thaliana*

For *Arabidopsis thaliana*, tissues of hypocotyl were removed from 10-day-old seedlings and preincubated in MS complete medium containing 0.5 mg/l 2,4-D and 0.5 mg/l kinetin for three days. The explants were immersed in $10^9$ cells/ml of *Agrobacterium tumefaciens* LBA4404 containing pBI121 for 20 min, and transferred to solid MS medium containing 500 mg/l carbenicillin, 50 mg/l kanamycin, and various ratios of 5-B-IAA/2iP or IAA/2iP for callus and shoot formation. Arabidopsis explants were incubated at 25° C., using an 18 h light/6 h dark cycle.

In transgenic *A. thaliana*, 5-B-IAA was a more effective auxin than IAA in promoting the regeneration of green callus.

TABLE 6

Effect of 5-bromoindole-3-acetic acid on the regeneration of green callus from Agrobacterium infected *Arabidopsis thaliana Landersburg* leaves.

| Type of auxin | % regeneration of green callus Ratio of Cytokinin (2iP)/auxin | | | |
|---|---|---|---|---|
| | 2.0 | 1.0 | 0.5 | 0.25 |
| IAA | 30% | 50% | 90% | 50% |
| 5-B-IAA | 70% | 100% | 80% | 70% |

As shown in Table 6, the effective range for cytokinin/auxin ratios was between approximately 2.0 and approximately 0.25. 100% green callus regeneration from transgenic *A. thaliana* was obtained at a 2iP/5-B-IAA ratio of 1.0.

Example 5

The use of 5-B-IAA for Stimulating the Regeneration of Transgenic Monocotyledonous Plants The transformation of monocotyledonous plants is carried out according to art-known methods as described by Wu, "Methods for Transforming Plant Cells," in *Plant Biotechnology* (1989), Kung and Arntzen, Eds., Butterworth Publishers, Stoneham, Mass. It is preferred that transformation of monocots such as rice and wheat be performed by the particle bombardment method as described in Wang et al. (1988) Plant Mol. Biol. 11:433–439. The regeneration of transformed monocots is performed according to known procedures (Vasil, Biotechnology (1988) 5:387–402) as described in Example 4.

For example, rice (*Oryza sativa*) is transformed using the particle bombardment method of Wang et al. (supra) or the Agrobacterium-mediating technique of Hiel et al. (1994) Plant Journal 6:271? or, alternatively, using the electroporation method as described by Dekeyser et al. (1990) Plant Cell 2:591–602. Regeneration of transformed rice is performed according to Abdullah et al. (1986) Bio/Technology 6:1087–1909 or, alternatively, according to Raineri et al. (1990) Bio/Technology 8:33–38.

In a further example, maize is transformed and regenerated according to the procedures of Rhodes et al. (1988) Bio/Technology 6:56–60 and (1988) Science 240:204–207.

In all cases, 5-B-IAA is used as the auxin to stimulate plant growth in accordance with the invention. Where required, one or more additional plant growth regulators may be added to the 5-B-IAA-comprising plant growth compositions.

All publications, patent applications and patents cited herein are incorporated by reference in the same extent as if each individual publication, patent application or patent was specifically and individually indicated to be incorporated by reference.

We claim:

1. A method for enhancing the growth of a plant comprising the step of growing said plant in the presence of a growth-enhancing, effective amount of a composition comprising 5-bromoindole-3-acetic acid, or a salt, an ester or an amide derivative thereof, such that an improvement in root formation occurs in said plant in the presence of said composition when compared to a corresponding plant in the absence of said composition.

2. The method of claim 1 wherein said composition further comprises one or more plant growth hormone.

3. The method of claim 1 wherein said composition comprises a cytokinin.

4. The method of claim 1 wherein said plant is a monocotyledon or a dicotyledon.

5. The method of claim 1 wherein said plant is a transgenic plant.

6. A method for regeneration of a plant from a plant cell or plant tissue which comprises the steps of:

(a) contacting said plant cell or plant tissue with an amount of 5-bromoindole-3-acetic acid effective for regeneration of roots; and (b) contacting said plant cell or plant tissue with a combination of 5-bromoindole-3-acetic acid and a cytokinin in a combined amount effective for the regeneration of callus or shoots from said plant cell or plant tissue.

7. The method of claim 6 wherein said plant cell or plant tissue comprises foreign DNA.

8. The method of claim 7 wherein foreign DNA has been introduced into said plant cell or plant tissue by particle bombardment.

9. The method of claim 8 wherein said plant cell or plant tissue is a cell or tissue of a monocotyledonous plant.

10. The method of claim 9 wherein said plant cell or plant tissue is a cell or tissue of a rice plant.

11. The method of claim 9 wherein said plant cell or plant tissue is a cell or tissue of maize.

12. The method of claim 6 wherein said cytokinin is kinetin, zeatin, $N^6$-($\Delta_2$ isopentyl) adenine, isopentenylpyrophosphate, or 6-benzylaminopurine.

13. A method for expediting regrowth in damaged plant tissues which comprises the step of contacting said damaged plant tissues with an amount of 5-bromoindole-3-acetic acid effective as a plant growth hormone.

14. A method for making a unwanted plant more susceptible to a herbicide which comprises the step of contacting said plant with an amount of 5-bromoindole-3-acetic acid effective for stimulating plant growth in combination with said herbicide.

* * * * *